(12) United States Patent
Van Herpen et al.

(10) Patent No.: US 7,541,603 B2
(45) Date of Patent: Jun. 2, 2009

(54) RADIATION SYSTEM AND LITHOGRAPHIC APPARATUS COMPRISING THE SAME

(75) Inventors: Maarten Marinus Johannes Wilhelmus Van Herpen, Heesch (NL); Vadim Yevgenyevich Banine, Helmond (NL); Derk Jan Wilfred Klunder, Geldrop (NL); Wouter Anthon Soer, Nijmegen (NL); Johannes Christiaan Leonardus Franken, Knegsel (NL); Olav Waldemar Vladimir Frijns, 's-Hertogenbosch (NL); Niels Machiel Driessen, Valkenswaard (NL)

(73) Assignee: ASML Netherlands B.V., Veldhoven (NL)

( * ) Notice: Subject to any disclaimer, the term of this patent is extended or adjusted under 35 U.S.C. 154(b) by 128 days.

(21) Appl. No.: 11/527,731

(22) Filed: Sep. 27, 2006

(65) Prior Publication Data

US 2008/0074655 A1    Mar. 27, 2008

(51) Int. Cl.
    *G21K 5/00* (2006.01)
(52) U.S. Cl. .................... 250/504 R; 101/450.1; 378/34
(58) Field of Classification Search ............ 250/504 R; 101/450.1, 451, 452; 378/34
    See application file for complete search history.

(56) References Cited

U.S. PATENT DOCUMENTS 4,692,884 A * 9/1987 Pryor .................... 250/205
2002/0037461 A1   3/2002 van der Werf et al.
2003/0146398 A1 * 8/2003 Schriever ............ 250/504 R
2004/0165160 A1   8/2004 van Beek et al.
2005/0254122 A1 * 11/2005 Fricke .................... 359/356
2006/0066824 A1   3/2006 Knappe et al.

FOREIGN PATENT DOCUMENTS

| EP | 1065568 A2 * | 1/2001 |
| EP | 1 202 117 A1 | 5/2002 |
| EP | 1 331 519 A2 | 7/2003 |
| EP | 1 471 385 A1 | 10/2004 |
| EP | 1 526 550 A1 | 4/2005 |
| EP | 1 530 091 A1 | 5/2005 |
| EP | 1 643 310 A1 | 4/2006 |
| WO | WO 2007/064210 A1 | 6/2007 |

OTHER PUBLICATIONS

Search Report and Written Opinion for International Application No. PCT/NL2007/050466 mailed Jun. 19, 2008, 10 pgs.

* cited by examiner

*Primary Examiner*—David P Porta
*Assistant Examiner*—Mark R Gaworecki
(74) *Attorney, Agent, or Firm*—Sterne, Kessler, Goldstein & Fox P.L.L.C.

(57) ABSTRACT

An optical sensor apparatus for use in an extreme ultraviolet lithographic system is disclosed. The apparatus includes an optical sensor comprising a sensor surface and a removal mechanism configured to remove debris from the sensor surface. Accordingly, dose and/or contamination measurements may be carried out conveniently for the lithographic system.

17 Claims, 5 Drawing Sheets

RADIATION SYSTEM AND LITHOGRAPHIC APPARATUS COMPRISING THE SAME

FIELD

The present invention relates to an optical sensor apparatus and a lithographic apparatus comprising the same. In an embodiment, the invention relates to an optical sensor apparatus for use in an extreme ultraviolet lithographic system.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In addition to EUV radiation, radiation sources used in EUV lithography typically generate contaminant material that is harmful for the optics and the working environment wherein the lithographic process is carried out. This is especially the case for an EUV source operating via a discharge produced laser induced plasma. Hence, in EUV lithography, a desire exists to limit the contamination of the optical system that is arranged to condition the beam of radiation coming from an EUV source. Furthermore, it may be desirable to be able to monitor the amount of contamination that is accumulating in the EUV system. Another desire may be to be able to monitor the amount of EUV energy generated by an EUV source.

SUMMARY

According to an aspect of the invention, there is provided an optical sensor apparatus for use in an extreme ultraviolet lithographic system comprising an optical sensor comprising a sensor surface and a removal mechanism configured to remove debris from the sensor surface.

According to an aspect of the invention, there is provided a method of detecting EUV radiation, comprising exposing a sensor surface of an optical sensor to an EUV source generating EUV radiation to detect the EUV radiation, and removing debris from the sensor surface.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
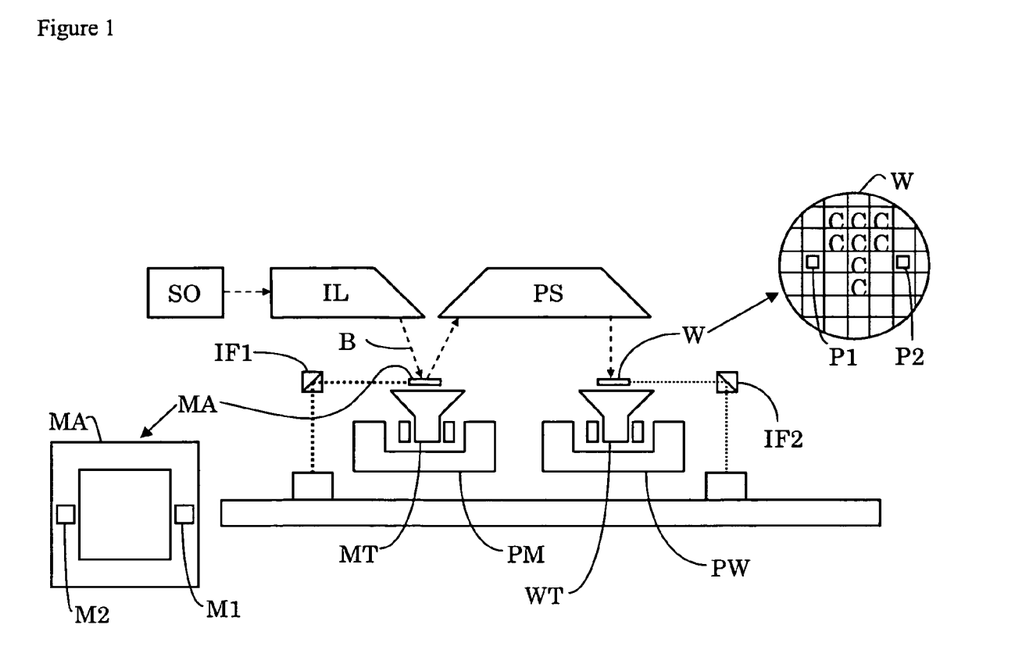
FIG. 1 depicts a lithographic apparatus according to an embodiment of the invention.

FIG. 1 schematically depicts a lithographic apparatus according to one embodiment of the invention. The apparatus comprises:

an illumination system (illuminator) IL configured to condition a radiation beam B (e.g. UV radiation or EUV radiation).

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PS configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a reflective type (e.g. employing a reflective mask). Alternatively, the apparatus may be of a transmissive type (e.g. employing a transmissive mask).

The lithographic apparatus may be of a type having two (dual stage) or more substrate tables (and/or two or more support structures). In such "multiple stage" machines the additional tables (and/or support structures) may be used in parallel, or preparatory steps may be carried out on one or more tables (and/or support structures) while one or more other tables (and/or support structures) are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system comprising, for example, suitable directing mirrors and/or a beam expander. In other cases the source may be an integral part of the lithographic apparatus, for example when the source is a mercury lamp. The source SO and the illuminator IL, together with the beam delivery system if required, may be referred to as a radiation system.

The illuminator IL may comprise an adjuster to adjust the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator and a condenser. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PS, which focuses the beam onto a target portion C of the substrate W. With the aid of the second positioner PW and position sensor IF2 (e.g. an interferometric device, linear encoder or capacitive sensor), the substrate table WT can be moved accurately, e.g. so as to position different target portions C in the path of the radiation beam B. Similarly, the first positioner PM and another position sensor IF1 can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
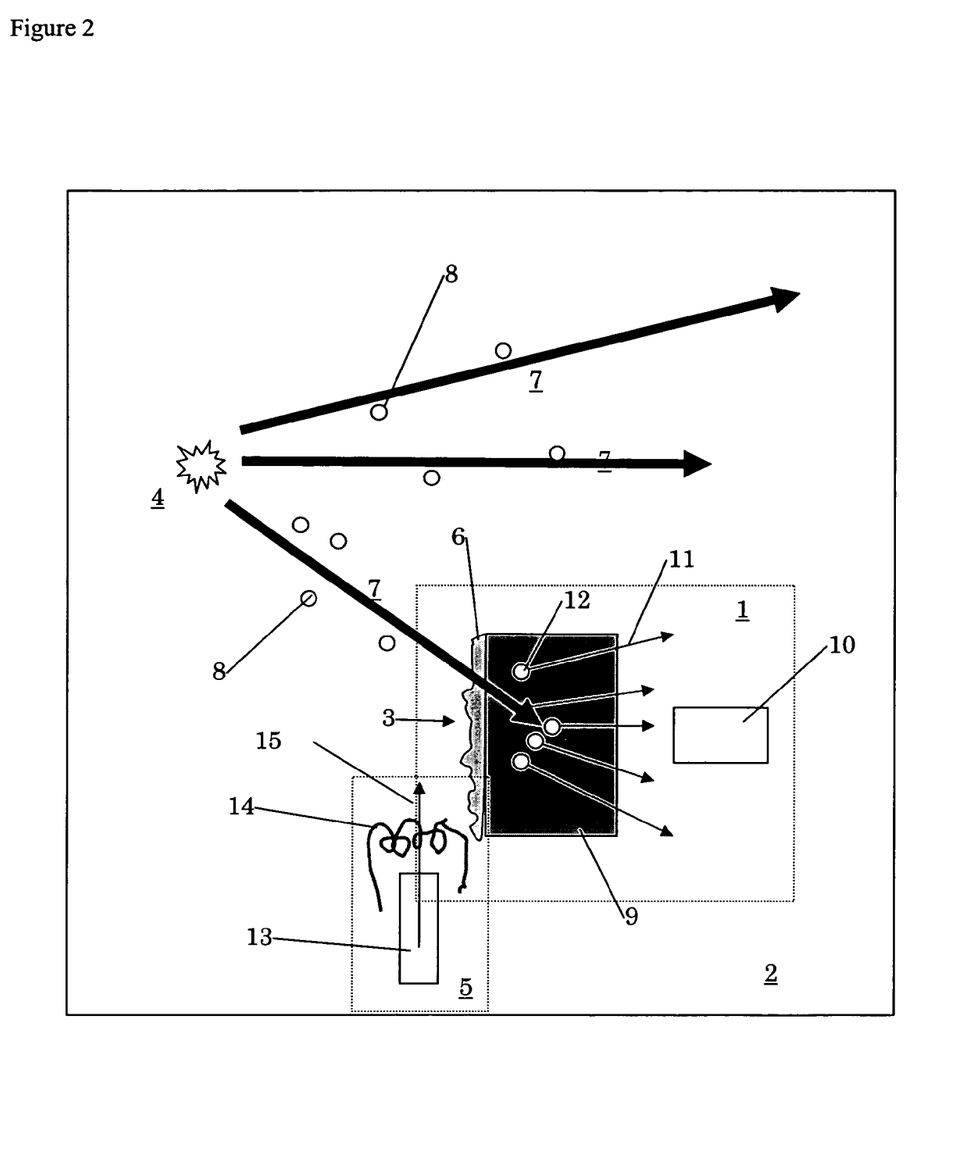
FIG. 2 depicts an embodiment of the invention.

In FIG. 2, an embodiment of the invention is shown. An optical sensor system 1 for an EUV radiation system 2 is shown, the sensor system 1 comprising a sensor surface 3 exposed to an EUV source 4. Furthermore, a removal mechanism 5 is shown and configured to remove a debris layer 6 from the sensor surface 3, the debris layer comprising, for example, Sn (typically when using a Sn EUV source) and/or other contaminants, such as carbon. Typically, the radiation system 2 comprises a discharge produced plasma source 4 such as a Sn or Xe source, however, another type of sources is possible. The source 4 depicted in FIG. 2 is typically operated in a pulsed way so that EUV radiation 7 is periodically generated in conjunction with debris 8 traveling from the source 4. Typical operating frequencies are in the range of several (tens of) kHz.

In the embodiment depicted in FIG. 2, the optical sensor system 1 comprises an EUV sensitive scintillation material 9 and a photo-detector 10 to receive electromagnetic radiation 11 from the scintillation material 9, the radiation 11 generated by scintillation 12 of the scintillation material 9 by incident EUV radiation 7. Although other materials may be possible, in an embodiment, the EUV sensitive scintillation material 9 comprises YAG:Ce. The YAG:Ce material accordingly converts EUV radiation to higher wavelength radiation, typically visible light radiation (blue) which is conventionally electronically converted using a photodiode or the like.

Although other cleaning methods, such as chemical cleaning or the like may be feasible, in an embodiment, the debris removal mechanism comprises a hydrogen radical supply system 5. Such a hydrogen radical supply system may comprise a hydrogen gas supply system 13 and a filament 14 or other means, such as a microwave or the like, known to the skilled person, to create radicals 15 from the supplied hydrogen gas molecules. In the shown embodiment, for example, this radical generator can be a hot filament at a temperature of, for example, 2000° C. Using cleaning with hydrogen radicals, it may be possible to provide a dose sensor that directly faces the EUV source.

In one mode of operation, the debris layer 6 may be intermittently removed from the sensor surface 3. In such an operation mode, the sensor can be used as a contamination detector that is occasionally cleaned, at certain interval times, or upon request, for example, when a certain threshold is reached that indicates that the photo-detector 10 is no longer, or is insufficiently receiving photonic energy 11. In such a mode of operation the degree of contamination can be monitored by deriving a thickness of a deposited debris layer 6 on the sensor surface, to be further clarified with reference to FIG. 4. In another mode of operation, the debris 8 may be continuously removed from the sensor surface 3, which means, that the removal mechanism is effectively active during the use of the optical sensor system 1, wherein the degree of contamination is kept at a certain level, desirably zero or a level, for example, from which reliably an incident dose of EUV energy can be determined by keeping the debris layer 6 substantially constant in thickness.

In the embodiment shown in FIG. 2, the advantage of using EUV radiation 7 is that specifically EUV radiation, in contrast to higher wavelength radiation, is highly sensitive to a thin contamination layer 5. Due to this, the previously described embodiment is most sensitive and will give the quickest response.

However, in some cases one may not need such a high sensitivity. In that case the YAG:Ce material 9 may be replaced by, for example, a piece of glass and a radiation beam of a longer wavelength, for example, in the range of UV—IR light can be used, generated by a separate radiation source (not shown), such as a LED. Such an embodiment may be cheaper and at the same time make the sensor less sensitive for contamination 8. Thus, this embodiment is suited for applications where contamination with a larger thickness is expected. This can be, for example, in a location near the EUV source, where source debris 8 is still amply present.

In an embodiment, the sensor may be placed at various locations in the EUV lithographic apparatus that are exposed to EUV radiation. For example, the sensor may be placed near the illuminator or projection optics in order to monitor the amount of contamination (e.g., carbon) growth on the optics and to have an alarm to alert of sudden increase in contamination growth (for example, due to a leak in the vacuum).

In an embodiment, the sensor may be placed near the EUV source, directly facing the EUV radiation and debris.

In an embodiment, the sensor is placed near the patterning device (e.g., mask), in order to monitor the amount of contamination accumulating on the patterning device. It is important that the patterning device remains clean, and therefore a monitor configured to detect the amount of contamination is advantageous here. For example, the patterning device may become contaminated due to out-gassing of the EUV resist.

Whether Sn contamination can be removed from a YAG sample using hydrogen radicals was tested and found to produce a high cleaning rate (may be more than 560 nm/hour). In an experiment, a circular (1 cm diameter) piece of YAG was used onto which a thin layer of 4.7 nm Sn was deposited using sputter deposition. Next, a thickness of the Sn layer was measured. Next the sample was exposed to hydrogen radicals using a hot-filament H radical source. The operating current was 22.0 A and the voltage was 21.0 V. The background pressure was 20.0 mbar and the temperature of the sample holder varied between 15 to 50° C. Table 1 shows the results of the experiment. In the total treatment time of 30 seconds, all Sn had been removed from the sample, corresponding to a cleaning rate of at least 4.7 nm/30 seconds=0.16 nm/s=564 nm/hour.

TABLE 1

| sample | Sn ($\mu g/cm^2$) | Sn (nm) |
|---|---|---|
| YAG before | 3.43 | 4.7 |
| YAG after | 0.01 | 0.01 |

Figure 3:
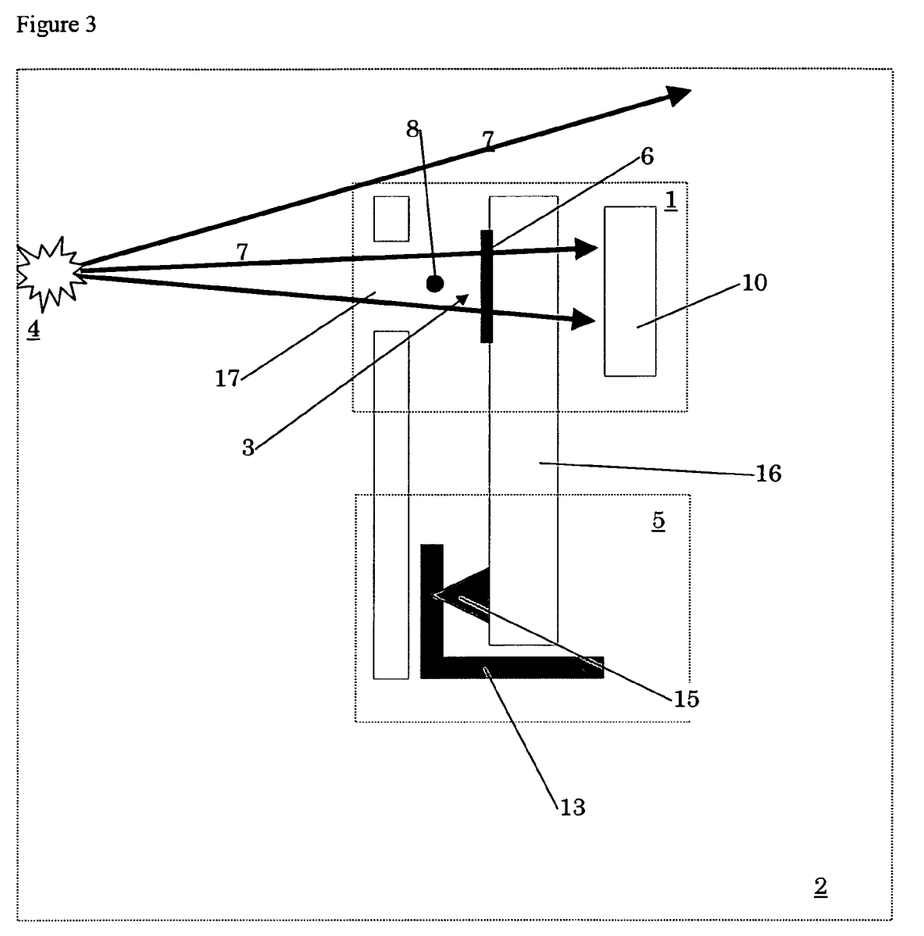
FIG. 3 depicts another embodiment of the invention.

FIG. 3 shows another embodiment of an optical sensor apparatus. In this embodiment, an EUV source 4 is depicted. Also, there is depicted an optical sensor system 1 and a debris removal mechanism 5. Here, a sensor surface 3 is a surface part of a rotatable EUV translucent plate 16. The removal mechanism 5 is arranged to remove debris 8 from another part of the translucent plate 16. The plate 16 may be rotated continuously or intermittently, wherein a part positioned in front of a detector 10 may be used as a spectral filter, and wherein the part positioned near the removal mechanism 5 is cleaned. Alternatively, the plate may be shifted or translated to move a portion exposed to debris toward the removal mechanism 5. In an embodiment, the EUV translucent plate 16 selectively passes radiation with wavelengths in a range of 10-20 nm. As an example, the EUV translucent plate 16 may comprise a Nb filter, a Zr/Si multilayer filter or a Zr/Nb multilayer filter. Likewise as in the embodiment depicted in FIG. 3, the application of this sensor system 1 may be used as, for example, a contamination monitor or as a dose sensing system.

According to an aspect of the invention, the embodiment of FIG. 3 uses a filter that stops Sn debris while still having some transmission for EUV (e.g., a 100 nm thick Nb filter has an EUV transmission of 62%) and the regular cleaning of the filter uses hydrogen cleaning. This can be done by rotating the filter 16 such that it passes through a cleaning station 5 each round trip and putting an aperture 17 before the filter 16 such that the detector 10 still experiences EUV, but the part of the filter that is not facing the detector is shielded from the source 4.

As a practical example, an EUV detector 1 according to the embodiment depicted in FIG. 3, is placed at a distance of 10 cm from the EUV source 4. The EUV source 4 typically generates an amount of debris equivalent to $10^{15}$-$10^{16}$ atoms per pulse. For a repetition frequency of 15 kHz, a total amount of atoms of $15*10^{18}$-$15*10^{19}$ per second is emitted equivalent to $2.5*10^{-5}$ to $2.5*10^{-4}$ mol of Sn (for a Sn EUV source). Accordingly, in this example, the flux of Sn atoms per unit area (at a distance of 10 cm) is $1.98*10^{-4}$ to $1.98*10^{-3}$ mol/$(m^2*s)$, corresponding with a deposited mass of Sn of $2.35*10^{-5}$ to $2.35*10^{-4}$ kg/$(m^2*s)$ and a layer thickness (density of Sn is $7.29*10^3$ kg/$m^3$) of 3.2 to 32 nm/s. Using this example, a typical Sn-cleaning rate would be between 3.2 to 32 nm/s or better, which is conceivable, for example, using a hydrogen cleaning method by supplying hydrogen radicals 15 from a hydrogen radical supply system 13 as illustrated in the embodiments of FIG. 2 and FIG. 3. Of course, the cleaning method is not restricted to this type of hydrogen cleaning but could be another cleaning method, such as halogen cleaning or the like.

In an embodiment where hydrogen cleaning is applied, desirably, the surface to be cleaned is provided with a cap layer having a hydrogen radical recombination constant less than 0.2, which, for example, may be provided by a $Si_3N_4$ layer. Such a cap layer may greatly improve the efficiency of hydrogen cleaning.

In addition, a rotation frequency Q is desirably chosen such that the time that the filter 16 is exposed to the radiation source 4, the exposure results in a Sn layer of about 0.8 nm thick, or, more generally, a thickness ranging from 0.4-2 nm. For a growth rate of about 32 nm/s, this would imply an exposure time of less than about 0.8/32=25 ms. With a typical value for an active sensor area 3 of 1 $cm^2$ this would then imply a linear velocity of more than about 0.01/0.025=0.4 m/s, which could correspond, for a typical radial distance between the center of the active area 3 of the EUV detector 1 and a center of rotation of 15 cm, to a rotation frequency of more than 0.4 Hz.

Figure 4:
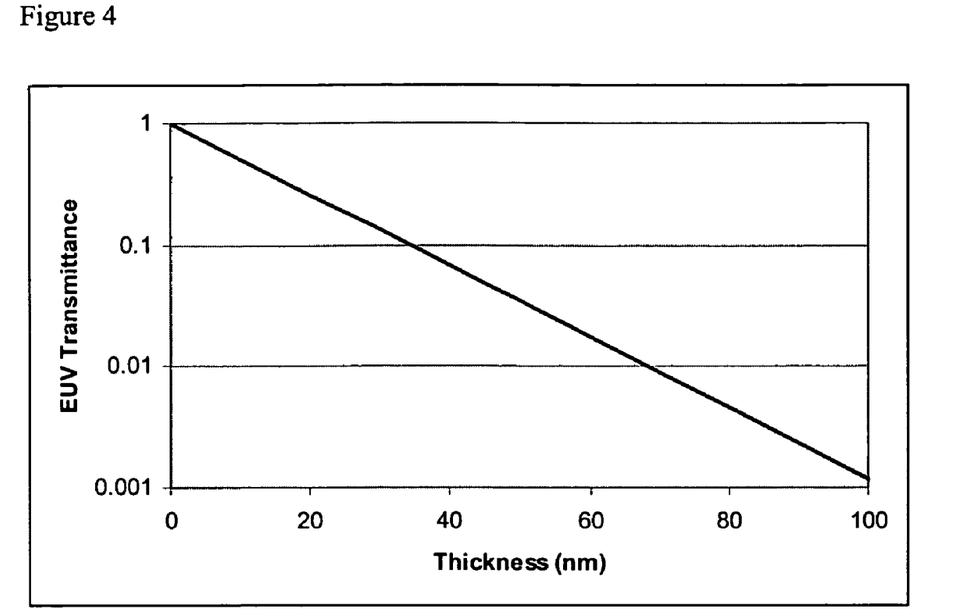
FIG. 4 depicts a graph illustrating a relation between an EUV transmittance ratio and a degree of contamination.

Referring to FIG. 4, a graph is illustrated showing a relation between EUV transmittance ratio and a degree of contamination. Accordingly, it is shown that there is almost an exponential relationship, wherein the transmittance, defined as a ratio of incident and transmitted energy, exponentially decreases with thickness of the debris layer 6. For example, a contamination thickness of 1 nm corresponds with a change in transmittance of 5%, which is an accuracy that is normally easy to achieve with a radiation sensor. For a 30 nm thickness, the transmittance ratio is about 0.1 and for a 100 nm thickness, the transmittance ratio is almost reduced to zero.

Accordingly, measurement of the transmittance ratio by the detector 10 is indicative of the amount of contamination, more specifically, of the thickness of the debris layer 6. Contamination may either accumulate slowly in time, or may grow instantly due to a problem, e.g., in the vacuum system (for example a leak in the vacuum tank). Continuous monitoring of the transmittance ratio detected by the optical sensor system 1 may therefore be a means for timely and adequate action to be taken upon detected irregularities such as a sudden increase in contamination. Furthermore, in an embodiment, the scintillation material is YAG:Ce having a conversion efficiency of around 2 to 3% (i.e., converting EUV radiation into visible light). Another material, CaS:Ce has a conversion efficiency of around 0.1 to 2% and is also suitable.

Figure 5:
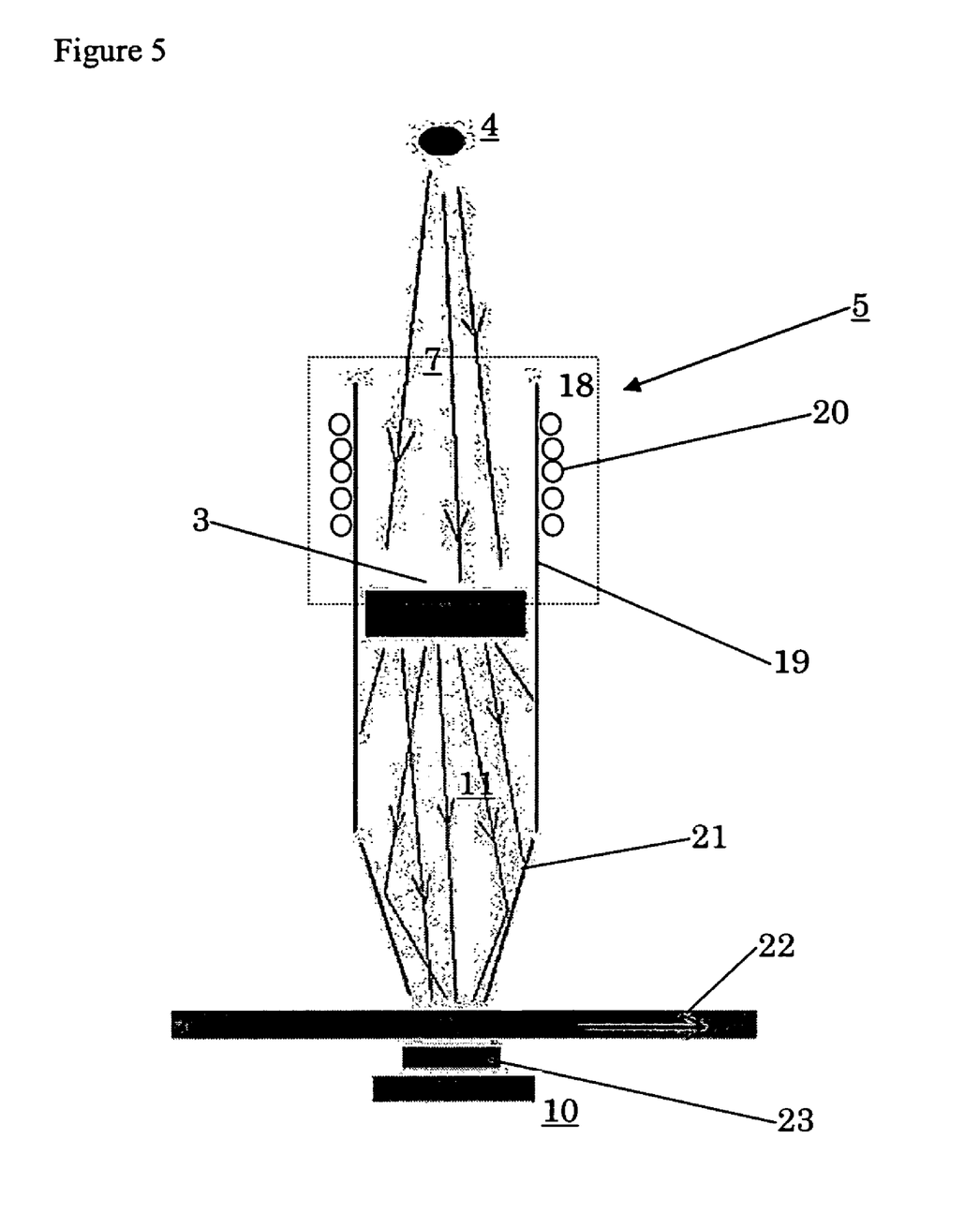
FIG. 5 depicts another embodiment of the invention.

FIG. 5 shows another embodiment of a removal mechanism 5 configured to remove debris 6 from the sensor surface 3. In this embodiment, the removal mechanism 5 comprises a heating system 18, to actively or passively elevate a temperature of the sensor surface 3. By elevating the temperature, a dynamic equilibrium may be reached wherein the amount of debris deposited can be matched to a debris evaporation rate, for example, in the case of Sn debris, such an elevation temperature would be more than about 900° C. to maximally about 1400° C. Accordingly, a continuous or semi-continuous state can be reached wherein over an extended time frame dose measurements or contamination measurements can be carried out. As an example, such as depicted in FIG. 5, the sensor surface may be surrounded by upstanding walls 19, comprising heating elements 20 configured to heat the walls 19. Additionally, these walls may be provided as a collimator 21 to collect and collimate light towards the sensor surface 3 and/or to the detector 10.

Further, for example, in the setup illustrated with reference to FIG. 5, a 10 mm flowing water layer 22 in combination with an IR absorbing glass filter 23 may be able to cool away 25.4 W and 1.6 W respectively (based on an estimated total of 27 W). The top-layer of the water flow can be sealed off using a broad-band spectral transmission filter, e.g. $MgF_2$, $SiO_2$ or $CaF_2$.

One or more of the embodiments herein may be used in the vicinity of an EUV source 4 substantially without further debris mitigation means provided in the pathway between the sensor system 1 and EUV source 4. However, depending on purpose, the sensor system 1 may be present further downstream of the radiation system 2, for example, in the vicinity of a contaminant trap (not shown). The contaminant trap may be a device that uses a high number of closely packed foils aligned generally parallel to the direction of transmission of the radiation generated by the EUV source. Contaminant debris 8, such as micro-particles, nano-particles and ions, can be trapped in the walls provided by the foil plates. Thus, such a foil trap functions as a contamination barrier trapping contaminant material from the source. Downstream from the foil trap, a collector may be present which functions to collect EUV radiation from the EUV source and focus the EUV radiation into a beam that is further conditioned downstream by projection optics. Thus, the collector converges the EUV radiation from the EUV source 4 to further EUV optics. Such a collector element may be cylindrically symmetric along a central axial direction and comprise concentrically curved shell formed reflective surfaces that are stacked at a distance ranging substantially between 1 and 7 cm. Alternatively, it may be of a multilayer normal incidence type.

Although one or more embodiments of the optical sensor apparatus described herein has been described as an apparatus located in the vicinity of the source, the sensor could also be used in further downstream optics, for instance to measure a contamination level of the system, in particular, for instance to measure carbon levels or the like. In such an embodiment, the sensor surface may not be directly exposed to the EUV radiation source but may be indirectly exposed, via one or more EUV reflecting mirrors.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. An optical sensor apparatus for use in an extreme ultraviolet lithographic system comprising:
    an optical sensor comprising a sensor surface; and
    a removal mechanism configured to remove debris from the sensor surface wherein (i) the sensor surface comprises a surface part of a rotatable plate and the removal mechanism is arranged to remove debris from another part of the plate or (ii) the removal mechanism comprises a heating system configured to elevate a temperature of the sensor surface.

2. The optical sensor apparatus according to claim 1, wherein the optical sensor comprises an EUV sensitive scintillation material and a detector configured to detect photonic energy emitted from the scintillation material in response to scintillation caused by incident EUV radiation.

3. The optical sensor apparatus according to claim 2, wherein the EUV sensitive scintillation material comprises YAG:Ce.

4. The optical sensor apparatus according to claim 1, wherein the sensor surface comprises a surface part of a rotatable plate, and wherein the removal mechanism is arranged to remove debris from another part of the plate.

5. The optical sensor apparatus according to claim 4, wherein the plate is an EUV translucent plate or an EUV sensitive scintillation material.

6. The optical sensor apparatus according to claim 5, wherein the EUV translucent plate is arranged to selectively transmit a spectral range of a beam of EUV radiation from the EUV source.

7. The optical sensor apparatus according to claim 5, wherein the EUV translucent plate selectively passes radiation with wavelengths in a range of 10-20 nm.

8. The optical sensor apparatus according to claim 5, wherein the EUV translucent plate comprises a Nb filter, a Zr/Si multilayer filter or a Zr/Nb multilayer filter.

9. The optical sensor apparatus according to claim 1, wherein the removal mechanism comprises a heating system configured to elevate a temperature of the sensor surface.

10. The optical sensor apparatus according to claim 9, wherein the elevation temperature is at least 900° C.

11. The optical sensor apparatus according to claim 9, wherein the sensor surface is surrounded by upstanding surrounding walls, comprising heating elements configured to heat the walls.

12. The optical sensor apparatus according to claim 1, wherein the EUV source is a laser induced plasma source or a discharge produced plasma source.

13. The optical sensor apparatus according to claim 12, wherein the plasma source comprises Sn or Xe.

14. A method of detecting EUV radiation, comprising:
    exposing a sensor surface of an optical sensor to an EUV source generating EUV radiation to detect the EUV radiation;
    removing debris from the sensor surface continuously, to provide a constant amount of debris deposited on the sensor surface; and
    calculating an EUV radiation energy level incident on the sensor surface.

15. The method according to claim 14, further comprising:
    deriving a radiation transmission ratio of radiation transmitted through a debris layer disposed on the sensor surface; and
    relating the transmission ratio to a degree of contamination of a radiation system.

16. The method according to claim 15, wherein the radiation transmitted through the debris layer is EUV radiation transmitted by the EUV radiation source.

17. The method according to claim 14, wherein the constant amount equals substantially zero.

* * * * *